(12) United States Patent
DeAngeli et al.

(10) Patent No.: US 8,057,753 B2
(45) Date of Patent: Nov. 15, 2011

(54) TEST STRIP EJECTION MECHANISM

(75) Inventors: Marco DeAngeli, Barzana (IT); Luca Valsecchi, Milan (IT)

(73) Assignee: LifeScan Scotland Limited (GB)

( * ) Notice: Subject to any disclaimer, the term of this patent is extended or adjusted under 35 U.S.C. 154(b) by 0 days.

(21) Appl. No.: 12/700,555

(22) Filed: Feb. 4, 2010

(65) Prior Publication Data

US 2011/0189062 A1 Aug. 4, 2011

(51) Int. Cl.
*G01N 21/75* (2006.01)
*G01N 21/00* (2006.01)
*B65D 81/00* (2006.01)
G01N 33/00 (2006.01)
G01N 33/52 (2006.01)
G01N 27/00 (2006.01)
A61B 5/00 (2006.01)

(52) U.S. Cl. ....... 422/401; 422/63; 422/82.05; 422/400; 422/402; 422/430; 204/400; 600/583; 600/584

(58) Field of Classification Search .......................... None
See application file for complete search history.

(56) References Cited

U.S. PATENT DOCUMENTS

| | | | |
|---|---|---|---|
| 5,266,179 A | 11/1993 | Nankai et al. | |
| 5,366,609 A | 11/1994 | White et al. | |
| 5,738,244 A | 4/1998 | Charlton et al. | |
| 5,831,820 A | 11/1998 | Huang | |
| 6,849,052 B2 | 2/2005 | Uchigaki et al. | |
| 6,916,159 B2 * | 7/2005 | Rush et al. | 417/321 |
| 7,138,089 B2 | 11/2006 | Aitken et al. | |
| 7,155,828 B2 | 1/2007 | Guimont et al. | |
| 7,264,139 B2 | 9/2007 | Brickwood et al. | |
| 7,337,918 B2 | 3/2008 | Fowler et al. | |
| 7,566,419 B2 | 7/2009 | Schulat et al. | |
| 2004/0035687 A1 * | 2/2004 | von Behrens et al. | 200/6 C |
| 2004/0138588 A1 * | 7/2004 | Saikley et al. | 600/583 |
| 2006/0099108 A1 * | 5/2006 | List et al. | 422/58 |
| 2007/0170200 A1 | 7/2007 | Chambers et al. | |

(Continued)

FOREIGN PATENT DOCUMENTS

| | | |
|---|---|---|
| EP | 1238632 | 5/2011 |
| WO | WO 2007/147494 A2 | 12/2007 |
| WO | WO 2009/055643 | 4/2009 |
| WO | WO 2009055643 A2 * | 4/2009 |

OTHER PUBLICATIONS

International Search Report, PCT/GB2011/000142, dated May 23, 2011, 11 pages.

(Continued)

*Primary Examiner* — Brian J Sines
*Assistant Examiner* — Jennifer Wecker (57) ABSTRACT

A test strip ejection mechanism, for use with a test strip receiving port and a test strip, includes a framework, an elongated shape memory alloy (SMA) strip (e.g., a SMA wire), a slider, and a heating module. The SMA strip has first and second ends that are attached to the framework and exhibits a solid state transition temperature. The slider is configured to travel along the framework. The heating module is configured to heat the SMA strip from a temperature below the solid state transition temperature to a temperature above the solid state transition temperature. Moreover, the SMA strip and slider are configured such that the slider travels along the framework under an applied force exerted on the slider by the SMA strip as the shape memory strip is heated from a temperature below the solid state transition temperature to a temperature above the solid state temperature by the heating module. In addition, the slider has a proximal end configured to engage a test strip received within a test strip receiving port and eject the test strip from the test strip receiving port as the slider travels along the framework. A test meter for use with a test strip includes a test strip receiving port and a test strip ejection mechanism.

11 Claims, 5 Drawing Sheets

U.S. PATENT DOCUMENTS

2008/0299009 A1 12/2008 Angelides
2009/0035120 A1* 2/2009 List .............................. 414/806
2009/0108013 A1 4/2009 Van Der Velde et al.
2009/0112155 A1 4/2009 Zhao et al.

OTHER PUBLICATIONS

International Search Report, PCT/GB2011/000143, dated Jun. 6, 2011, 11 pages.

* cited by examiner

TEST STRIP EJECTION MECHANISM

The present invention is related to the following co-pending U.S. application: U.S. patent application Ser. No. 12/700,570, filed on Feb. 4, 2010.

BACKGROUND OF THE INVENTION

1. Field of the Invention

The present invention relates, in general, to medical devices and, in particular, to test strip ejection mechanisms, related test meters and related methods.

2. Description of Related Art

The determination (e.g., detection and/or concentration measurement) of an analyte in a fluid sample is of particular interest in the medical field. For example, it can be desirable to determine glucose, ketones, cholesterol, acetaminophen and/or HbA1c concentrations in a sample of a bodily fluid such as urine, blood or interstitial fluid. Such determinations can be achieved using analyte test strips, based on, for example, photometric or electrochemical techniques, along with an associated test meter.

During use, a single test strip is typically inserted into a test meter. Following determination of an analyte in a bodily fluid sample applied to the test strip, the test strip is removed from the test meter and discarded. Conventional approaches to inserting and removing a test strip from a test meter are described in, for example, U.S. Pat. Nos. 5,266,179; 5,366,609; and 5,738,244; and U.S. Patent Application Publication 2009/0108013, each of which is hereby incorporated in full by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings, in which like numerals indicate like elements, of which:

DETAILED DESCRIPTION OF ILLUSTRATIVE EMBODIMENTS

The following detailed description should be read with reference to the drawings, in which like elements in different drawings are identically numbered. The drawings, which are not necessarily to scale, depict exemplary embodiments for the purpose of explanation only and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

In general, a test strip ejection mechanism, for use with a test strip receiving port and a test strip, includes a framework, an elongated shape memory alloy (SMA) strip (e.g., a SMA wire), a slider, and a heating module. The SMA strip has first and second ends that are attached to the framework and exhibits a solid state transition temperature. The slider is configured to travel along the framework.

The heating module is configured to heat the SMA strip from a temperature below the solid state transition temperature to a temperature above the solid state transition temperature. Moreover, the SMA strip and slider are configured such that the slider travels along the framework under an applied force exerted on the slider by the SMA strip as the SMA strip is heated from a temperature below the solid state transition temperature to a temperature above the solid state temperature. In addition, the slider has a proximal end configured to engage a test strip received within a test strip receiving port and eject the test strip from the test strip receiving port as the slider travels along the framework.

Shape memory alloys (SMA) are materials that that transform from a deformed shape (also referred to herein as a "deformed configuration") to an original shape (also referred to herein as a "programmed configuration") upon heating to a temperature above their solid-state transformation temperature. This behavior is also referred to as returning to their original shape (programmed configuration).

At temperatures below the solid state transformation temperature, the shape memory alloy Nitinol is in the martensite phase. To set a Nitinol SMA strip (e.g., a Nitinol SMA wire) to a predefined "programmed configuration" or programmed state, the SMA strip is held in the programmed configuration and heated to approximately 500° C., at which temperature atoms of the SMA strip arrange themselves into the austenite phase. Thereafter, when heated above the solid state transition temperature, the Nitinol SMA wire will automatically revert from the martensite phase to the austenite phase, which acts to change the shape memory alloy (via a solid-state phase transition) from any deformed configuration back into the programmed configuration. In other words, the shape memory alloy strip changes shape in response to temperature. During such a transformation, the SMA exerts a smooth and controlled force that is employed in embodiments of the present invention to eject a test strip.

Once apprised of the present disclosure, one skilled in the art will recognize that there are a variety of shape memory alloys that may be suitable for use test strip ejection mechanisms according to embodiments of the present invention depending on their solid state transition temperature and mechanical properties. Known shape memory alloy materials include, for example:

Nickel/Titanium alloys (including Nickel/Titanium alloys commercially available as Nitinol and Tinel);
Copper/Zinc/Aluminum alloys
Copper/Aluminum/Nickel alloys
Silver/Cadmium alloys
Gold/Cadmium alloys
Copper/Tin alloys
Copper/Zinc alloys
Indium/Titanium alloys
Nickel/Aluminum alloys
Iron/Platinum alloys
Manganese/Copper alloys
Iron/Manganese/Silicon alloys Test strip ejection mechanisms according to embodiments of the present invention are beneficial in that they operate automatically. In other words, they operate with minimal human intervention, in the absence of human energy (as opposed to conventional manual ejection mechanisms) and in a manner essentially independent of external influence or control. Test strip ejection mechanisms according to embodiments of the present invention also beneficially provide test strip ejection without the need for human handling of, and potential contamination from, the test strip. The test strip ejection mechanisms are also compact and relatively quiet due to the absence of ejection-related motors and/or gears and are, therefore, suitable for incorporation into handheld portable test meters (such as test meters for the determination of glucose).

Figure 1:
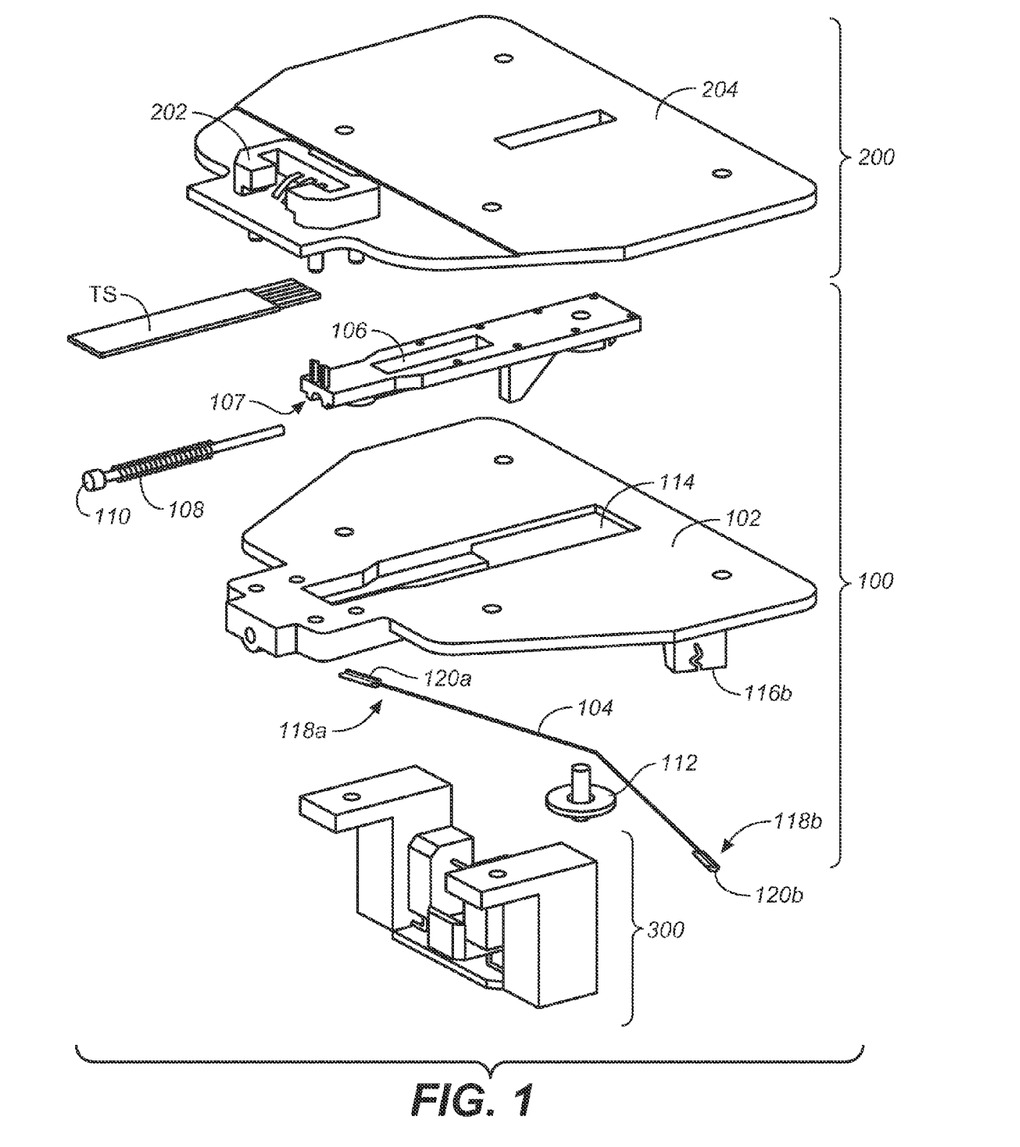
FIG. 1 is a simplified exploded view of a test strip ejection mechanism according to an embodiment of the present invention in use with a test strip receiving port assembly and optical module of a test meter and a test strip.
Figure 2A:
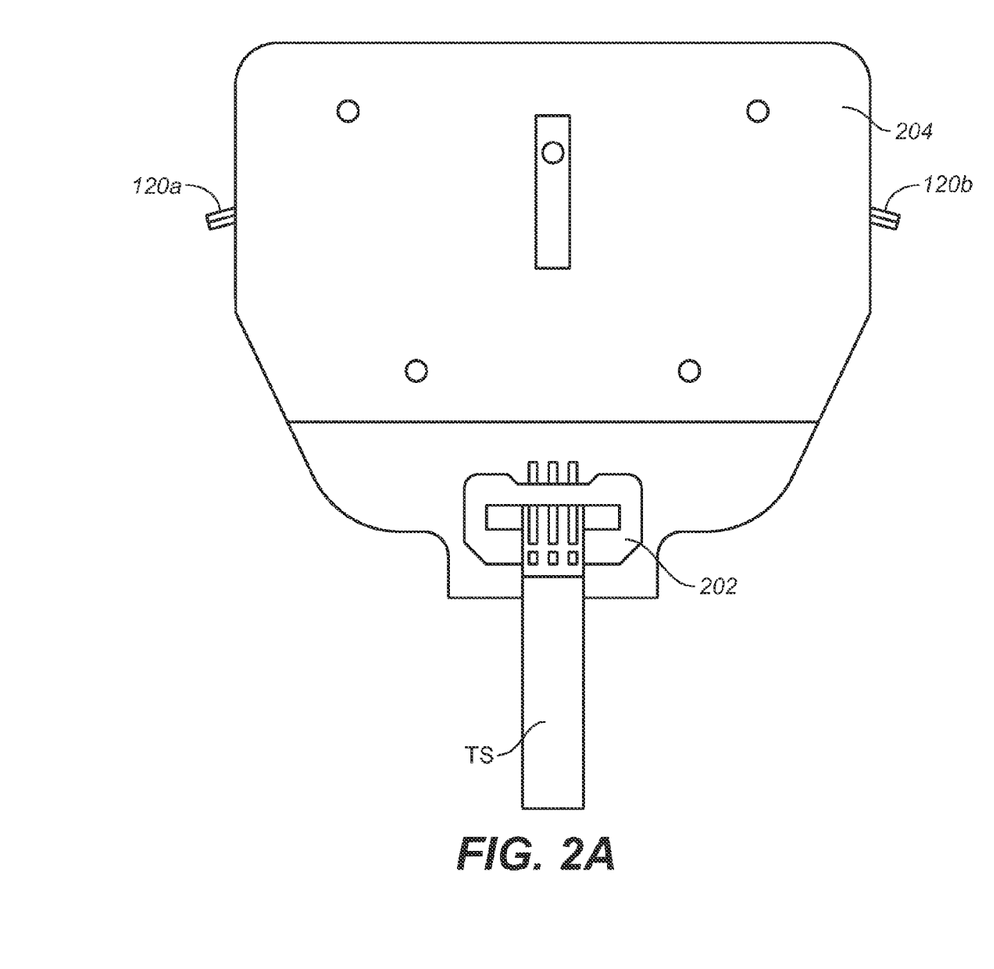
FIGS. 2A, 2B and 2C are simplified top, side and bottom views of the test strip ejection mechanism of FIG. 1 in use with the test strip receiving port assembly, optical module and test strip of FIG. 1.
Figure 2B:
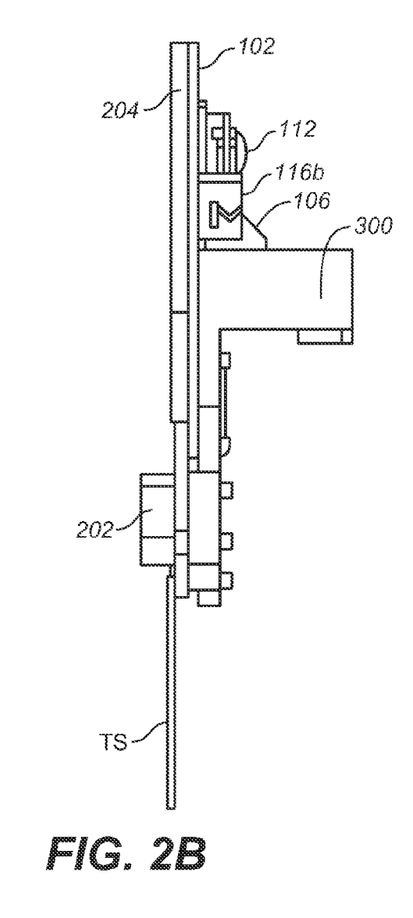
Figure 2C:
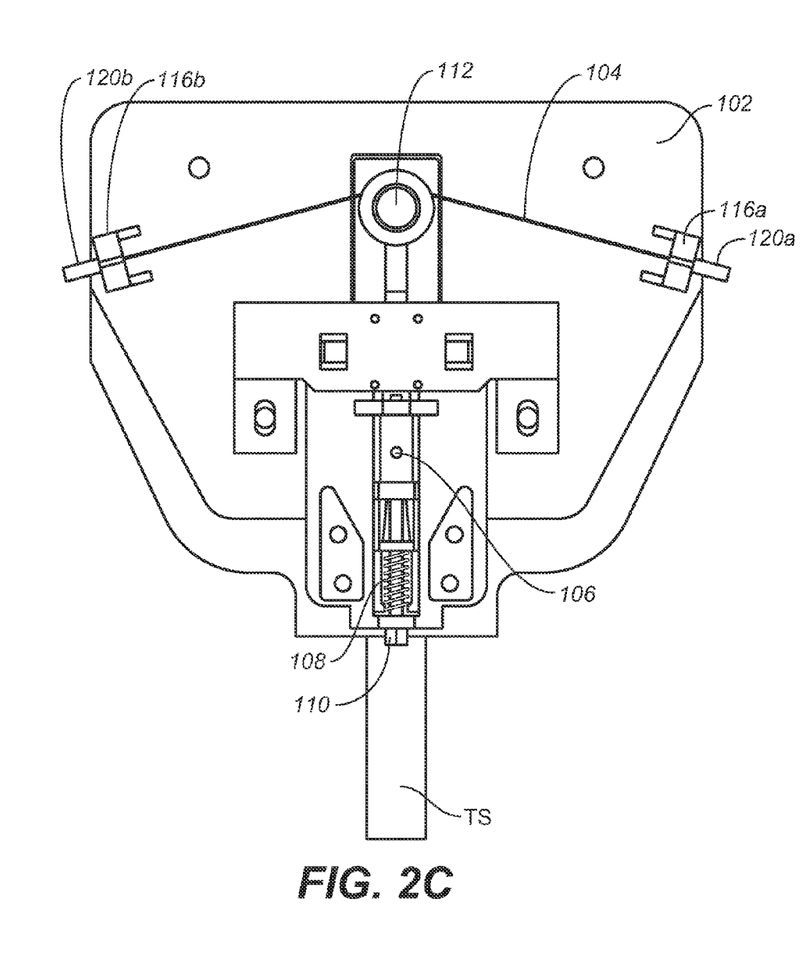
Figure 3:
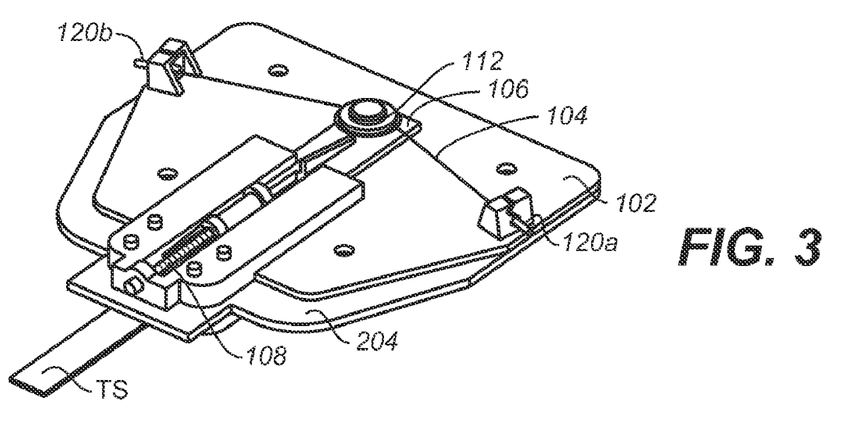
FIG. 3 is a simplified perspective view (from the bottom) of test strip ejection mechanism of FIG. 1 in a pre-ejection state with the test strip receiving port assembly, optical module and test strip of FIG. 1.
Figure 4:
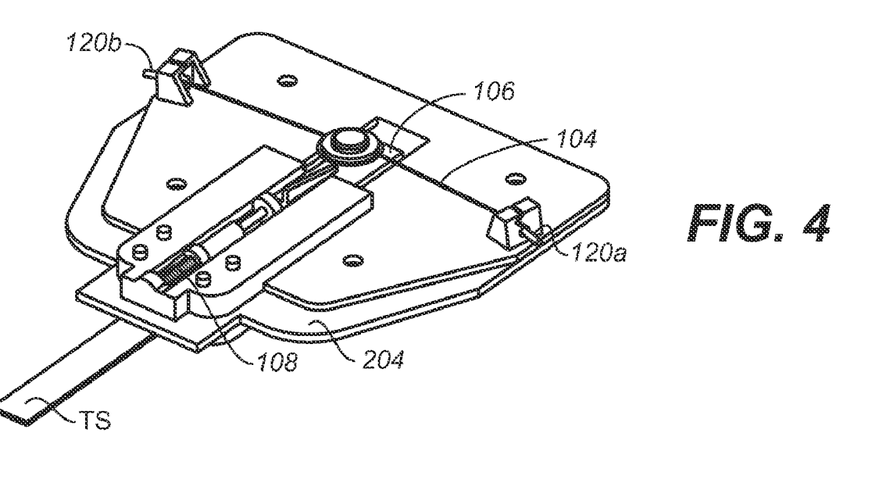
FIG. 4 is a simplified perspective view (from the bottom) of test strip ejection mechanism of FIG. 1, with the test strip receiving port assembly, optical module and test strip of FIG. 1, during ejection of the test strip.
Figure 5:
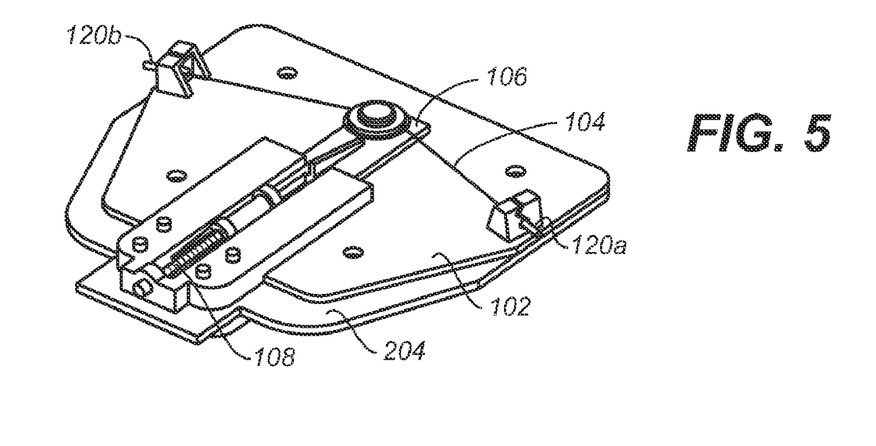
FIG. 5 is a simplified perspective view (from the bottom) of test strip ejection mechanism of FIG. 1, with the test strip receiving port assembly, optical module and test strip of FIG. 1, following ejection of the test strip and deformation of the shape alloy memory strip.

FIG. 1 is a simplified exploded view of a test strip ejection mechanism 100 according to an embodiment of the present invention in use with a test strip receiving port assembly 200 and optical module 300 of an associated test meter and a test strip TS. FIGS. 2A, 2B and 2C are simplified top, side and bottom views of test strip ejection mechanism 100 in use with test strip receiving port assembly 200, optical module 300 and test strip TS. FIG. 3 is a simplified perspective view (from the bottom) of test strip ejection mechanism 100 in a pre-ejection state (for example, following strip insertion and analyte determination). FIG. 4 is a simplified perspective view (also from the bottom) of test strip ejection mechanism 100 during ejection of test strip TS with the shape memory alloy strip in a programmed configuration. FIG. 5 is a simplified perspective view of test strip ejection mechanism 100 following ejection of test strip TS and return of the shape alloy memory strip to a deformed configuration.

Referring to FIGS. 1, 2A through 2C, 3, 4 and 5, test strip ejection mechanism 100 is configured for use with test strip receiving port assembly 200 and test strip TS. Test strip ejection mechanism 100 includes a framework 102, an elongated shape memory wire 104, a slider 106, spring 108, spindle 110, and connector 112 (i.e., a screw and washer combination). Test strip ejection mechanism 100 also includes a heater module, which for simplicity is not shown in FIGS. 1, 2A through 2C, 3, 4 and 5. The heater module can be any suitable heater module known to those of skill in the art including, for example, a heater module configured to force a predetermined electrical current through elongated shape memory alloy wire 104 in a controllable manner and, thereby, heat the elongated shape memory alloy wire.

Test strip receiving port assembly 200 includes a test strip receiving port 202 and test strip receiving framework 204. Optical module 300 is configured to sense the presence and absence of a test strip in test strip receiving port assembly 200. Optical module 300 can be any suitable optical module known to those of skill in the art and can include, for example, a an LED-based light source and a photodiode-based light receiver configured to detect the presence or absence of a test strip based on, for example, the position of an opaque light-blocking fin or reflector optionally included in slider 106. Such detection can be employed, if desired, to automatically control the deactivation of elongated shape memory alloy wire 104 and/or to monitor for mechanical failures of test strip ejection mechanism 100. Alternatively, a suitable mechanical switch can also be employed to detect the presence or absence of a test strip based on, for example, the position of slider 106.

As knowledge of the presence or absence of a test strip can be used for test meter purposes (e.g., to initiate analyte determination by the test meter) or to conclude (deactivate) heating of an elongated shape memory alloy wire within the test strip ejection mechanism once a test strip has been ejected, optical module 300 can be considered either a component of the test meter or an optional component of the test strip ejection mechanism.

Framework 102 is attached to the test strip receiving port assembly 200 and includes a slider guide slot 114 and strip attachment slots 116a and 116b. Elongated shape memory alloy wire 104 has a longitudinal axis, a first end 118a and a second end 118b. First end 118a second end 118b of elongated shape memory alloy 104 are constrained by attachment to framework 102 via strip attachment slots 116a and 116b and crimps 120a and 120b of elongated shape memory alloy wire 104.

As described above, elongated shape memory alloy wire 104 inherently exhibits a solid state transition temperature due to being formed of a suitable shape memory alloy material (e.g., a Nickel/Titanium alloy). In embodiments of the present invention, the solid state transition temperature is typically in a range between 65° C. and 95° C. The lower temperature of the range is predetermined to be greater than the maximum ambient temperature encountered during normal use and the upper temperature of the range is chosen based on thermal compatibility with materials used to construct framework 102, slider 106 and other components of the test strip ejection mechanism (e.g., plastic materials). Upon heating above the solid state transition temperature, the shape memory behavior of elongated shape memory alloy wire 104 results in a shrinkage ratio in the range of, for example, 1% to 3%.

In test strip ejection mechanism 100, elongated shape memory alloy wire 104 has a typical but non-limiting diameter of 0.2 mm and length of 55.8 mm and can be constructed of a shape memory alloy containing, for example, 54% Nickel and 46% Titanium. Such an elongated shape memory alloy wire can be heated from room temperature to above its solid state transition temperature with a 3% contraction by, for example, forcing a 0.5 amp current through the elongated shape memory alloy wire for a time duration in the range of approximately 1.0 seconds to 1.2 seconds.

During transition from a deformed configuration to a pre-programmed configuration (i.e., upon heating from below the solid state transition temperature to above the solid state transition temperature, see FIGS. 3 and 4 in particular), this dual-ended constraint of the elongated shape memory alloy wire in conjunction with the deformed configuration of the pre-ejection state and the predefined programmed configuration results in the production of a force that is exerted on the slider. The exertion of the force results in test strip ejection.

In the embodiment of FIGS. 1-5, the shape memory alloy wire is in a deformed configuration when the shape memory alloy strip is at a temperature below the solid state transition temperature (e.g., an ambient room temperature of approx.

25° C.) and the shape memory alloy strip is in a programmed configuration when the shape memory alloy strip is heated to a temperature above the solid-state transition temperature (for example, above 65° C.). In addition, in the embodiment of test strip ejection mechanism 100, the longitudinal axis of the shape memory alloy wire in the deformed configuration is in essentially an equilateral obtuse-angled triangle configuration (see FIGS. 1, 2C, 3 and 5) and the longitudinal axis of the shape memory alloy strip in the programmed configuration is in an essentially straight-line configuration (see FIG. 4) perpendicular to a test strip ejection direction. These predefined configurations serve to produce a smooth linear movement in the slider during ejection of a test strip.

The equilateral obtuse-angled triangle configuration of the shape memory alloy wire is a "bowed" configuration that transitions to a straight-line configuration while functioning to push slider 106 and eject a test strip. These configurations and functions are reminiscent of the configuration and function of a bow and arrow. In a bow and arrow analogy, which is presented for non-limiting descriptive purpose only, the framework and elongated shape memory alloy wire are reminiscent of the bow and bow string, while the slider and test strip are reminiscent of the arrow. However, once apprised of the present disclosure, one skilled in the art will recognize that test strip ejection mechanisms according to embodiments of the present invention operate automatically, beneficially employ shape memory alloy behavior and have other unique, non-obvious and beneficial aspects that differ from a conventional bow and arrow.

In the embodiment of test strip ejection mechanism 100, slider 106 is configured to travel along framework 102 in slider guide slot 114 (see FIG. 1 in particular) and provides a mechanical connection between elongated shape memory alloy wire 104 and test strip TS. In particular, slider 106 has a proximal end 107 configured to engage test strip TS received within test strip receiving port 202 and eject test strip TS from test strip receiving port 202 as slider 106 travels along framework 102 (see FIGS. 3, 4 and 5 in particular). The distance of slider movement during ejection of a test strip is, for example, in the range of 4 mm.

Spring 108 and spindle 110 are configured to return and hold the shape memory alloy strip in a deformed configuration when the shape memory alloy strip is at a temperature below the solid state transition temperature (see FIGS. 3 and 5 in particular) and enable the shape memory alloy strip to move to a programmed configuration when the shape memory alloy strip is heated to a temperature above the solid-state transition temperature (see FIG. 4 in particular). Spring 108 and spindle 110 can be configured to exert suitable operational forces on the elongated shape memory alloy wire during operation of test strip ejection mechanism 100. For example, a force of approximately 1N in a nearly unloaded state and a maximum force of 3.2N during compression of spring 108 can be exerted during operation. Connector 112 is configured to hold (along with spring 108 and strip attachment slots 116a and 116b) elongated shape memory alloy wire 104 in the deformed configuration on framework 102. Connector 112 also provides mechanical contact between elongated shape memory alloy wire 104 and slider 106.

The heating module (not depicted in the FIGs.) of test strip ejection mechanism 100 is configured to heat the shape memory alloy strip from a temperature below the solid state transition temperature to a temperature above the solid state transition temperature. Such heating can be accomplished, be employing a heating module that forces an electrical current through the shape memory alloy wire with the heating occurring as a consequence of electrical resistive thermal effects.

In test strip ejection mechanism 100, elongated shape memory alloy wire 104 and slider 106 are configured such that slider 106 travels along framework 102 under an applied force exerted on slider 106 by elongated shape memory alloy wire 104 as the shape memory strip is heated by the heating module (not shown). The heating raises the temperature of the elongated shape memory alloy wire 104 from a temperature below the solid state transition temperature (e.g., ambient room temperature) to a temperature above the solid state temperature.

A benefit of test strip ejection mechanisms according to embodiments of the present invention is that there is no need to include mechanisms that translate a rotational movement into a linear test strip ejection movement. Test strip ejection mechanisms according to embodiments of the present invention are also beneficially thin; lightweight; low cost, relatively silent and eject test strips in a smooth manner.

In general, test meters for use with a test strip (e.g., a test strip configured for the determination of glucose in a whole blood sample by photometric or electrochemical-based techniques) according to embodiments of the present invention include a test strip receiving port and a test strip ejection mechanism. Moreover, the test strip ejection mechanism includes a framework, an elongated shape memory alloy (SMA) strip, a slider, and a heating module.

The SMA strip of the test strip ejection mechanism has first and second ends that are constrained by attachment to the framework and the SMA strip exhibits a solid state transition temperature. Moreover, the slider is configured to travel along the framework and the heating module is configured to heat the SMA strip from a temperature below the solid state transition temperature to a temperature above the solid state transition temperature. In addition, the SMA strip and slider are configured such that the slider travels along the framework under an applied force exerted on the slider by the SMA strip as the shape memory strip is heated from a temperature below the solid state transition temperature to a temperature above the solid state temperature by the heating module. In addition, the slider has a proximal end configured to engage a test strip received within a test strip receiving port and eject the test strip from the test strip receiving port as the slider travels along the framework.

Figure 6:
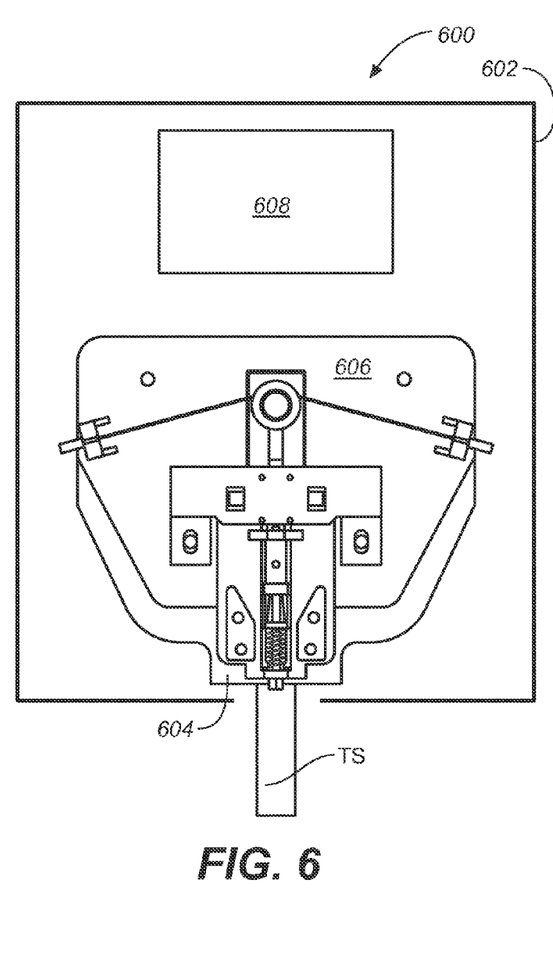
FIG. 6 is a simplified block diagram of a test meter according to an embodiment of the present invention.

FIG. 6 is a simplified block diagram of a test meter 600 according to an embodiment of the present invention. Test meter 600 includes a housing 602, a test strip receiving port 604 configured to receive, and have ejected therefrom, a test strip (TS), a test strip ejection mechanism 606 (for example, test strip ejection mechanism 100 as described with respect to FIGS. 1, 2A-2C, 3, 4 and 5) and a signal processing module 608.

Test strip ejection mechanism 606 includes the following components (not shown in FIG. 6) as described elsewhere herein: (i) a framework attached to test strip receiving port 604; (ii) an elongated shape memory alloy strip with a longitudinal axis, a first end and a second end, the first end and second end attached to the framework; (iii) a slider configured to travel along the framework; and (iv) a heating module configured to heat the shape memory alloy wire from a temperature below the shape memory alloy's solid state transition temperature to a temperature above the shape memory alloy's solid state transition temperature.

In addition, and as described further elsewhere herein, the shape memory alloy strip and slider are configured in a manner that the slider travels along the framework under an applied force, with the applied force being exerted on the slider by the shape memory alloy strip as the shape memory alloy strip is heated from a temperature below the solid state transition temperature to a temperature above the solid state temperature by the heating module. Moreover, the slider has a proximal end configured to engage test strip TS (that has been received within test strip receiving port 604) and eject test strip TS from test strip receiving port 604 as the slider travels along the framework.

Signal processing module 608 is configured to measure and process a signal (electrical, optical or a combination thereof) during analyte determination. One skilled in the art will appreciate that signal processing module 608 can include and employ a variety of sensors and circuits that are not depicted in simplified FIG. 6 during determination of an analyte.

Test meters according to embodiments of have multiple beneficial and unique characteristics including, for example, (i) being relatively simple and inexpensive due to the absence of bulky and complicated motor-based test strip ejection systems; (ii) automatic ejection of a test strip (i.e., the test strip ejection occurs with minimal or no human intervention); (iii) being nearly silent during test strip ejection due to a minimum number of moving components; and (iv) providing smooth and controlled ejection of a test strip based on controlled shape transformation of a constrained shape memory alloy strip.

In addition, once apprised of the present disclosure, one skilled in the art will recognize that test meters according to embodiments of the present invention can incorporate any of the features, components, techniques, benefits and characteristics of test strip ejection mechanisms and methods for ejecting a test strip from a test meter according to embodiments of the present invention and described herein.

Figure 7:
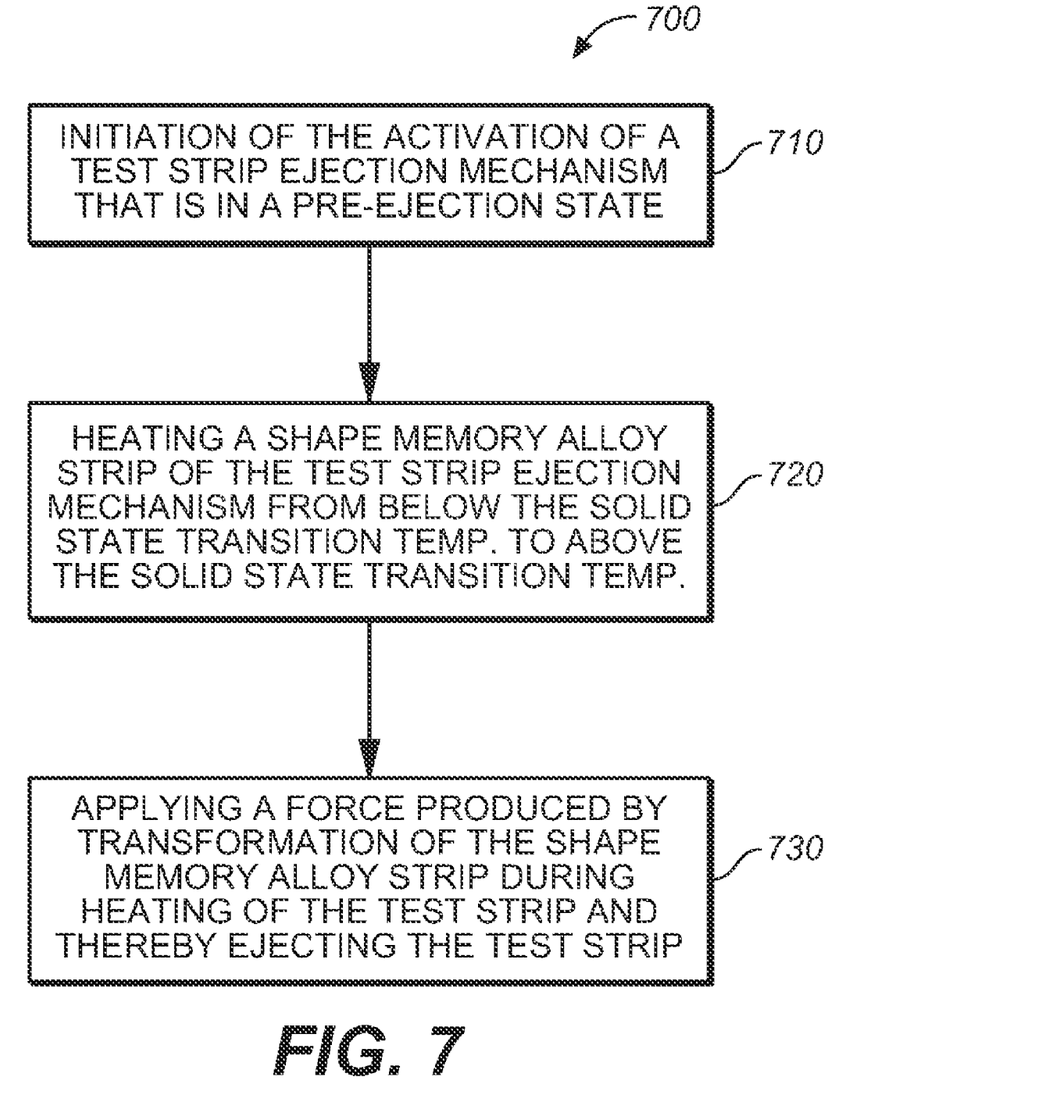
FIG. 7 is a flow diagram depicting stages in a method for ejecting a test strip from a test meter according to an embodiment of the present invention.

FIG. 7 is a flow diagram depicting stages in a method 700 for ejecting a test strip from a test meter according to an embodiment of the present invention. At step 710 of method 700, activation of a test strip ejection mechanism of a test meter that is in a pre-ejection state is initiated. In method 700, the test strip ejection mechanism includes a shape memory alloy strip that exhibits a solid state transition temperature. Moreover, the shape memory alloy strip (e.g., a shape memory alloy wire made of a Nickel-Titanium shape memory alloy) has a programmed configuration and a deformed configuration. In addition, in the test strip ejection mechanism pre-ejection state, a test strip (e.g., a test strip configured for the determination of glucose in a whole blood sample) has been received within a test strip receiving port of the test meter and the shape memory alloy strip is in the deformed configuration.

The initiating step can be accomplished, for example, by a user pressing an initiating button of the test meter or by suitable electronic modules and/or software that senses the completion of analyte determination by the test meter. Once apprised of the present disclosure, suitable electronic modules and software that can accomplish such initiation will be apparent to those of skill in the art.

Method 700 also includes heating, in response to the initiation step, the shape memory alloy strip from below the solid state transition temperature to above the solid state transition temperature, as set forth in step 720 of FIG. 3. The heating of step 720 results in the shape memory alloy strip undergoing a transformation from the deformed configuration to a programmed configuration.

At step 730, the method also includes applying a force produced by the transformation from the deformed configuration to the programmed configuration to the test strip and, thereby, ejecting the test strip from the test strip receiving port of the test meter.

Once apprised of the present disclosure, one skilled in the art will recognize that method 700 can be readily modified to incorporate any of the techniques, benefits and characteristics of test strip ejection mechanisms and test meters according to embodiments of the present invention and described herein.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that devices and methods within the scope of these claims and their equivalents be covered thereby.

What is claimed is:

1. A test meter for use with a test strip, the test meter comprising:
   a test strip receiving port configured to receive, and have ejected therefrom, a test strip;
   a test strip ejection mechanism that includes:
      a framework attached to the test strip receiving port;
      an elongated shape memory alloy strip with a longitudinal axis, a first end and a second end, the first end and second end attached to the framework, the shape memory alloy strip exhibiting a solid state transition temperature;
      a slider configured to travel along the framework;
      a heating module configured to heat the shape memory alloy wire from a temperature below the solid state transition temperature to a temperature above the solid state transition temperature; and
   a test strip receiving port framework;
   wherein the shape memory alloy strip and slider are configured such that the slider travels along the framework under an applied force exerted on the slider by the shape memory alloy strip as the shape memory strip is heated by the heating module from a temperature below the solid state transition temperature to a temperature above the solid state temperature; and
   wherein the slider has a proximal end configured to engage a test strip received within the test strip receiving port and eject the test strip from the test strip receiving port as the slider travels along the framework, and
   wherein the test strip receiving port and test strip ejection mechanism are attached to the test strip receiving port framework.

2. The test meter of claim 1 further including:
   an optical sensor module attached to the framework; and
   a signal processing module.

3. The test meter of claim 1 wherein the test strip ejection mechanism further includes:
   a spring configured to return and hold the shape memory alloy strip in a deformed configuration when the shape memory alloy strip is at a temperature below the solid state transition temperature and enable the shape memory alloy strip to move to a programmed configuration when the shape memory alloy strip is heated to a temperature above the solid-state transition temperature.

4. The test meter of claim 3 wherein the test strip ejection mechanism further includes:
a spindle, and
wherein the spring is disposed around the spindle in an annular configuration and the spring exerts a force on the slider via the spindle.

5. The test meter of claim 1 wherein the shape memory alloy strip is in a deformed configuration when the shape memory alloy strip is at a temperature below the solid state transition temperature and the shape memory alloy strip is in a programmed configuration when the shape memory alloy strip is heated to a temperature above the solid-state transition temperature.

6. The test meter of claim 5 wherein the longitudinal axis of the shape memory alloy in the deformed configuration is in essentially a bowed configuration and the longitudinal axis of the shape memory alloy strip in the programmed configuration is in an essentially a straight-line configuration.

7. The test meter of claim 6 wherein the straight-line configuration is essentially perpendicular to a test strip ejection direction.

8. The test meter of claim 1 wherein the heating module is configured to heat the shape memory alloy strip by forcing an electrical current through the shape memory alloy strip.

9. The test meter of claim 1 wherein the shape memory alloy strip is a shape memory alloy wire.

10. The test meter of claim 9 wherein the shape memory alloy wire is a Nickel-Titanium shape memory alloy wire.

11. The test meter claim 1 wherein the test strip ejection mechanism further includes:
a first crimp; and
a second crimp, and
wherein the first end and second ends of the shape memory alloy strip are attached to the framework via the first crimp and a second crimp, respectively.

* * * * *